(12) United States Patent
Kitajima et al.

(10) Patent No.: US 6,534,281 B2
(45) Date of Patent: Mar. 18, 2003

(54) IMMUNOASSAY FOR MEASURING HUMAN C-PEPTIDE AND KIT THEREFOR

(75) Inventors: Sachiko Kitajima, Tokyo (JP); Yoshihiro Kurano, Tokyo (JP); Kaoru Nakatsubo, Tokyo (JP); Isao Nishizono, Tokyo (JP)

(73) Assignee: Fujirebio Inc., Tokyo (JP)

( * ) Notice: Subject to any disclaimer, the term of this patent is extended or adjusted under 35 U.S.C. 154(b) by 70 days.

(21) Appl. No.: 09/878,380

(22) Filed: Jun. 12, 2001

(65) Prior Publication Data

US 2002/0160435 A1 Oct. 31, 2002

(30) Foreign Application Priority Data

Jun. 12, 2000 (JP) ......................................... 2000-174691

(51) Int. Cl.⁷ .................. C07K 14/00; C07K 14/62; C07K 14/625
(52) U.S. Cl. .................. 435/7.92; 435/7; 435/7.21; 435/7.92; 435/7.1; 435/68; 435/71; 435/272; 435/212; 435/213; 435/240.1; 435/320.1; 435/288.4; 436/546; 436/172; 436/518; 436/800; 436/809; 436/811; 436/532; 436/175; 436/533; 436/534; 424/93.21
(58) Field of Search ........................... 435/7, 7.1, 7.21, 435/7.92, 68, 71, 272, 212, 213, 240.1, 320.1, 288.4; 436/546, 172, 518, 800, 809, 811, 532, 175, 533, 534; 424/93.21

*Primary Examiner*—Christopher L. Chin
*Assistant Examiner*—Lisa V. Cook
(74) *Attorney, Agent, or Firm*—Birch, Stewart, Kolasch & Birch, LLP

(57) ABSTRACT

An immunoassay for selectively measuring human C-peptide as well as a kit therefor is disclosed. In the method, human C-peptide contained in a sample, a first anti-human C-peptide antibody, and a second anti-human C-peptide antibody which is immobilized on a solid support are reacted to form an immune complex among these three components. The formed immune complex is separated from the non-reacted antibodies and sample; and then the separated immune complex is quantified. The first antibody recognizes an epitope existing in the region from 1st to 16th amino acid residue from the N-terminal of the human C-peptide, and the second antibody recognizes an epitope existing in the region from 1st to 16th amino acid residue from the N-terminal of human C-peptide; with the proviso that the first and second antibodies do not recognize the same epitope so that they can simultaneously bind to said human C-peptide.

19 Claims, 8 Drawing Sheets

Synthetic Fragments of Human C-peptide: N-terminal Region

| | Arg -2 | Arg -1 | Glu 1 | Ala 2 | Glu 3 | Asp 4 | Leu 5 | Gln 6 | Val 7 | Gly 8 | Gln 9 | Val 10 | Glu 11 | Leu 12 | Gly 13 | Gly 14 | Gly 15 | Pro 16 |
|---|---|---|---|---|---|---|---|---|---|---|---|---|---|---|---|---|---|---|
| N-1 | -2 | | | | | | | | | | | | | | | | | |
| N-2 | -2 | 1 | | | | | | | | | | | | | | | | |
| N-3 | | | 1 | | | | | | | 8 | | | | | | | | |
| N-4 | | | | | 3 | | | | | 8 | | | | 12 | | | | |
| N-5 | | | | | 3 | | | | | 8 | | | | | | | | |
| N-6 | | | | 2 | | | 5 | | | 8 | | | | | | | | |
| N-7 | | | | | 3 | | | | | | | 10 | | | | | | |
| N-8 | | | | | | 4 | | | | | | 10 | | | | | | |
| N-9 | | | | | | | | | 7 | | 9 | | | | | 14 | | |
| N-10 | | | | | | | | | 7 | | | | | | | | | 16 |
| N-11 | | | | | | | | | 7 | | | | | 12 | 13 | | | |
| N-12 | | | | | | | | | | 8 | 9 | | | | | 14 | | |
| N-13 | | | | | | | | | | | | | | | | 14 | | |
| N-14 | | | | | | | | | | | | 10 | | | | 14 | | |

Fig. 1

C-terminal Region of Synthetic Human C-peptide

|   | Leu | Ala | Leu | Glu | Gly | Ser | Leu | Gln | Lys | Arg |
|---|-----|-----|-----|-----|-----|-----|-----|-----|-----|-----|
|   | 24  | 25  | 26  | 27  | 28  | 29  | 30  | 31  | 31+1 | 31+2 |
| C-1 | 24 | | | | | | | | | 31+2 |
| C-2 | 24 | | | | | | | 31 | | |
| C-3 | 24 | | | | | 29 | | | | |

CPT3F11 N1-N7 Binding Assay (B)

CPT3F11 C1-C3 Binding Assay (A)

9101 N1-N7 Binding Assay (B)

9101 C1-C3 Binding Assay (A)

(B)

(A)

9103 N1-N7 Binding Assay (B)

9103 C1-C3 Binding Assay

US 6,534,281 B2

IMMUNOASSAY FOR MEASURING HUMAN C-PEPTIDE AND KIT THEREFOR

BACKGROUND OF THE INVENTION

I. Field of the Invention

The present invention relates to a method for measuring human C-peptide and a kit therefor.

II. Description of the Related Art

Human C-peptide is a peptide consisting of 31 amino acids, and is a constituent of proinsulin which is an insulin precursor. More particularly, human C-peptide is a polypeptide which is a decomposition product released simultaneously with insulin into the blood when insulin is formed by cleavage of proinsulin by an endopeptidase. The amino acid sequences of human proinsulin and human C-peptide are shown in SEQ ID NOs: 1 and 2, respectively, in the Sequence Listing.

Human proinsulin is a polypeptide consisting of 86 amino acids, and mainly composed of insulin B chain constituted by 1st to 30th amino acids, C-peptide constituted by 33rd to 63rd amino acids, and insulin A chain constituted by 66th to 86th amino acids. Thus, C-peptide is bound to insulin B chain through the 31st amino acid Arg and 32nd amino acid Arg, and is bound to insulin A chain through the 64th amino acid Lys and 65th amino acid Arg. As mentioned above, C-peptide is released into the blood simultaneously with insulin when proinsulin is subjected to processing for yielding insulin. Thus, C-peptide serves as an index of secretion kinetics of insulin, and the kinetics of blood C-peptide can be an important index for investigation of ability to secrete endogenous insulin in patients suffering from diabetes. In fact, measurement of C-peptide is used for diagnosis and therapy of diabetes, and is useful for diagnosis of insulinoma and insulin autoimmune syndrome.

Usually, the ratio of C-peptide to proinsulin is about 1:0.6–1.3 in healthy individuals, about 1:0.3–0.5 in pyknic type individuals, and about 1:5 in patients suffering from islet cell adenoma. It has been reported that this ratio fluctuates depending on the conditions of the disease and on the diets, and C-peptide excess state and proinsulin excess state can exist (P.N.A.S., 67, 148–155, 1970). In cases where the amount of cross-reactive substance is small, large cross-reactivity of the measurement system may not be problematic very much. However, in cases where the amount of the cross-reactive substance (i.e., proinsulin in case of C-peptide) is large, and where the abundance ratio therebetween may largely fluctuate, the measured value is not reliable as an index representing the pathological or healthy conditions. For example, in cases where the blood level of C-peptide is periodically monitored for therapy, the influence by proinsulin which is a cross-reactive substance cannot be disregarded. Thus, a system for measuring C-peptide which has a low cross-reactivity to proinsulin is strongly demanded.

For measuring C-peptide, competition immunoassays using polyclonal antibodies to C-peptide have been mainly employed. For example, Japanese Patent Publication (Kokoku) No. 57-44663 discloses a competition immunoassay using radiolabeled C-peptide, and Japanese Laid-open Patent Application (Kokai) No. 1-165962 discloses a competition immunoassay using C-peptide labeled with an enzyme. However, the detection sensitivities of C-peptide by these methods are not high, the cross reactivities with proinsulin are also high, and the reproducibilities are poor, so that an improvement thereof is needed. As a method which improved these competition immunoassays, Japanese Laid-open Patent Application (Kokai) No. 4-177166 discloses a sandwich immunoassay for measuring C-peptide using a monoclonal antibody. Although detection sensitivity was improved a little by this method, the detection sensitivity is still not satisfactory. Further, cross-reactivity was not improved by this method. Thus, a method which attains low cross-reactivity does not exist so far.

Since the linear structure of C-peptide is completely included in the linear structure of proinsulin, it has been believed that it is difficult for an immunoassay for measuring C-peptide to eliminate cross-reactivity to proinsulin.

SUMMARY OF THE INVENTION

Accordingly, an object of the present invention is to provide an immunoassay for measuring human C-peptide by which the cross-reactivity to proinsulin is low, which has a high reproducibility and high detection sensitivity, as well as to provide a kit for carrying out the immunoassay.

The present inventors thought that although the linear structure of C-peptide is completely included in the linear structure of proinsulin, C-peptide may be specifically measured if an antibody which recognizes a terminal region of C-peptide is used because the terminals of C-peptide are exposed unlike proinsulin so that the structure and/or electric conditions of the terminals of C-peptide may be different from those of the corresponding regions in proinsulin. Based on this concept, the present inventors intensively studied to discover that by sandwich immunoassay using a first anti-human C-peptide antibody which recognizes an epitope existing in the region from 1st to 10th amino acid residue from the N-terminal of the human C-peptide, and a second anti-human C-peptide antibody which is immobilized on a solid support and which recognizes an epitope existing in the region from 1st to 16th amino acid residue from the N-terminal of the human C-peptide, the first and second antibodies recognizing different epitopes so that they can simultaneously bind to human C-peptide, C-peptide may be selectively measured avoiding cross-reactivity to human proinsulin, thereby completing the present invention.

That is, the present invention provides a method for measuring human C-peptide comprising the steps of:

(i) reacting human C-peptide contained in a sample, a first anti-human C-peptide antibody or an antigen-binding fragment thereof, and a second anti-human C-peptide antibody or an antigen-binding fragment thereof immobilized on a solid support to form an immune complex among three components;

(ii) separating the formed immune complex from non-reacted antibodies and/or antigen-binding fragments thereof, and sample, and (iii) quantifying the separated immune complex;

the first antibody recognizing an epitope existing in the region from $1^{st}$ to $10^{th}$ amino acid residue (residues 1–10 of SEQ ID NO:2) from the N-terminal of the human C-peptide; the second antibody recognizing an epitope existing in the region from $1^{st}$ to $16^{th}$ amino acid residue (residues 1–16 of SEQ ID NO:2) from the N-terminal of the human C-peptide; and the first and second antibodies recognizing different epitopes so that they can simultaneously bind to the human C-peptide.

The present invention also provides a kit for measuring human C-peptide comprising:

(a) a first vessel containing a first anti-human C-peptide antibody or an antigen-binding fragment thereof, which is labeled; and (b) a second vessel containing a solid support on which a second anti-human C-peptide antibody or an antigen-binding fragment thereof immobilized;

the first antibody recognizing an epitope existing in the region from $1^{st}$ to $10^{th}$ amino acid residue (residues 1–10 of SEQ ID NO:2) from the N-terminal of the human C-peptide; the second antibody recognizing an epitope existing in the region from $1^{st}$ to $16^{th}$ amino acid residue (residues 1–16 of SEQ ID NO:2) from the N-terminal of the human C-peptide; and the first and second antibodies recognizing different epitopes so that they can simultaneously bind to the human C-peptide.

BRIEF DESCRIPTION OF THE DRAWINGS

FIG. 1 shows the positions of fragments of human C-peptide (residues 31–48 of SEQ ID NO:1), which fragments were used for determining epitopes of the antibodies used in Examples;.

FIG. 2 shows the positions of fragments of human C-peptide (residues 56–65 of SEQ ID NO:1), which fragments were used for determining epitopes of the antibodies used in Examples;

DETAILED DESCRIPTION OF THE PREFERRED EMBODIMENTS

Figure 3:
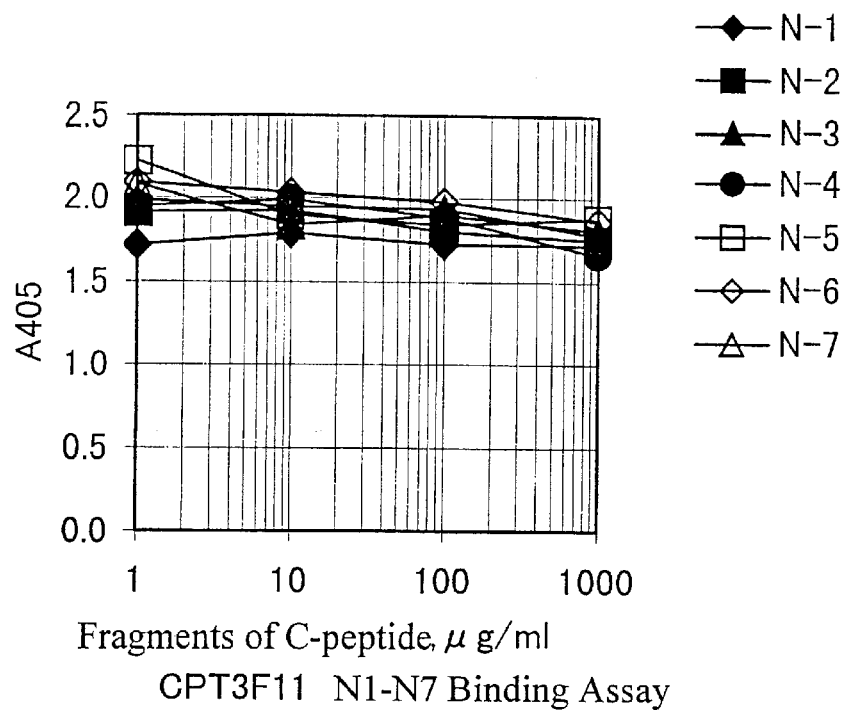
FIG. 3 shows the results of binding inhibition assay for anti-human C-peptide antibody CPT3F11 using various fragments of human C-peptide.
Figure 3:
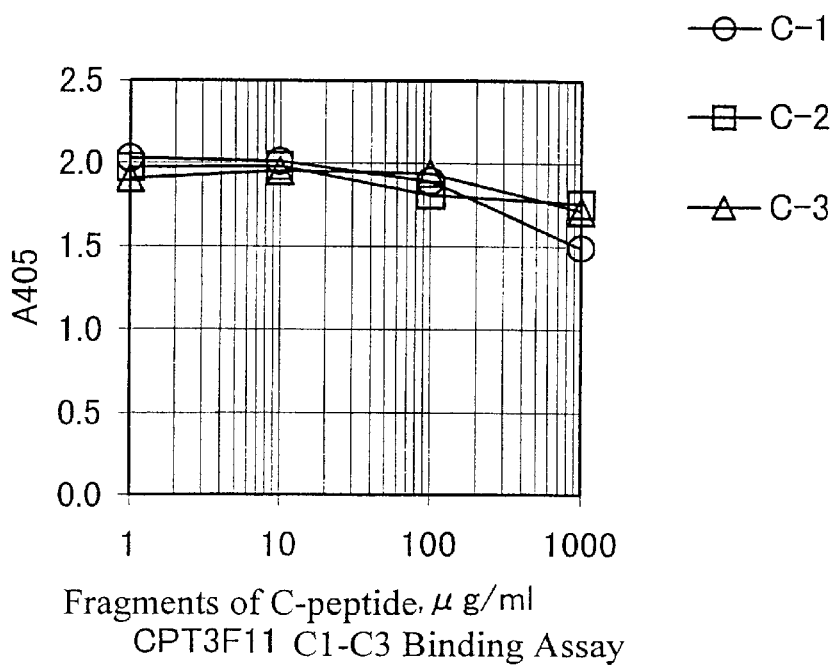
Figure 4:
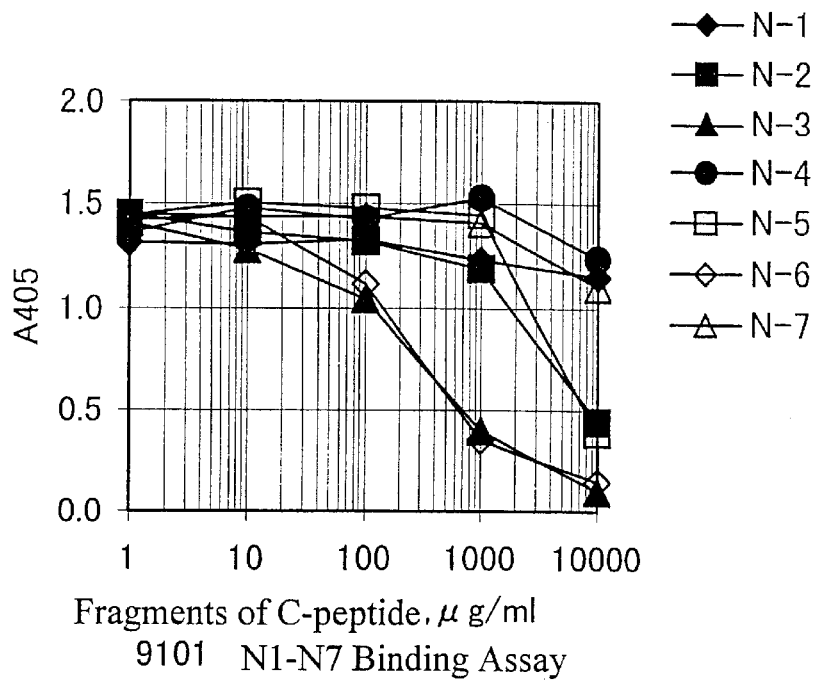
FIG. 4 shows the results of binding inhibition assay for anti-human C-peptide antibody 9101 using various fragments of human C-peptide.
Figure 4:
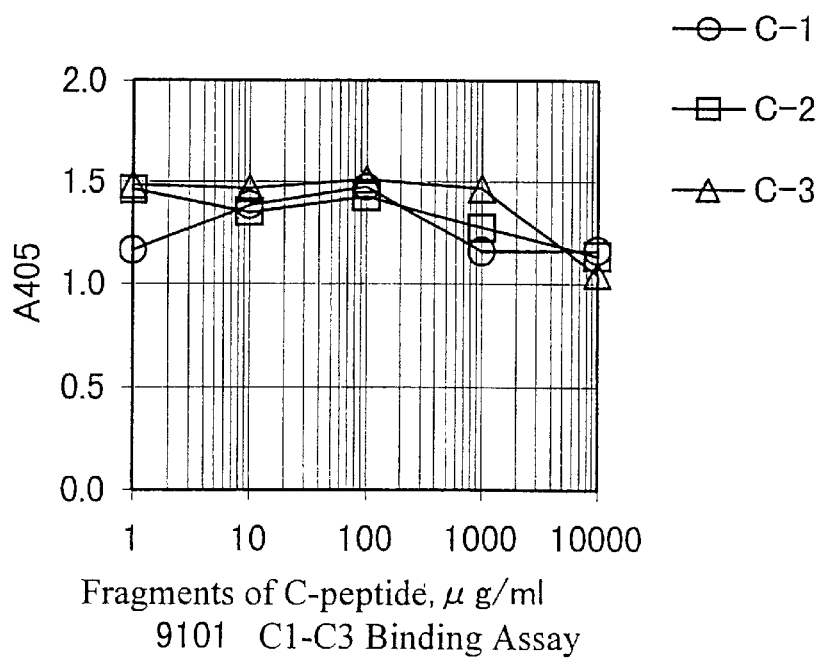
Figure 5:
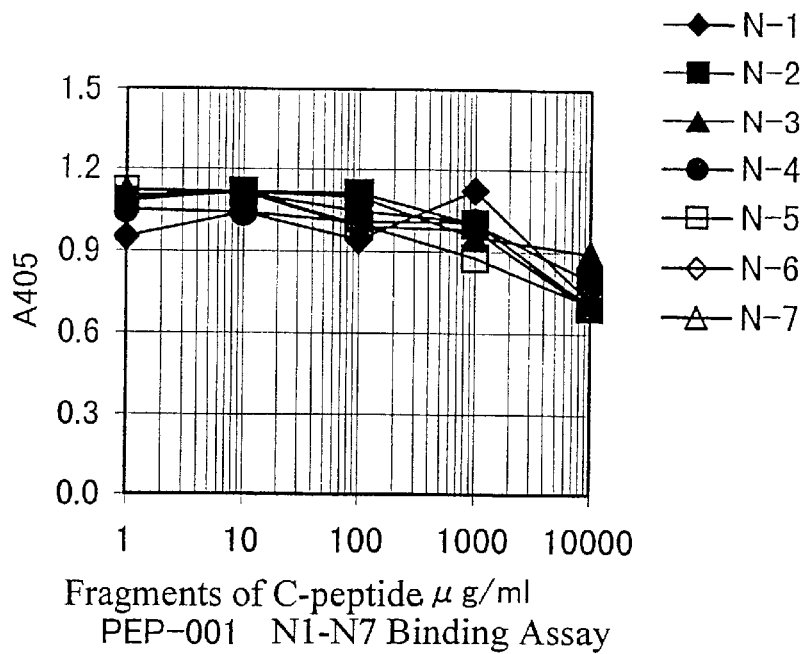
FIG. 5 shows the results of binding inhibition assay for anti-human C-peptide antibody PEP-001 using various fragments of human C-peptide.
Figure 5:
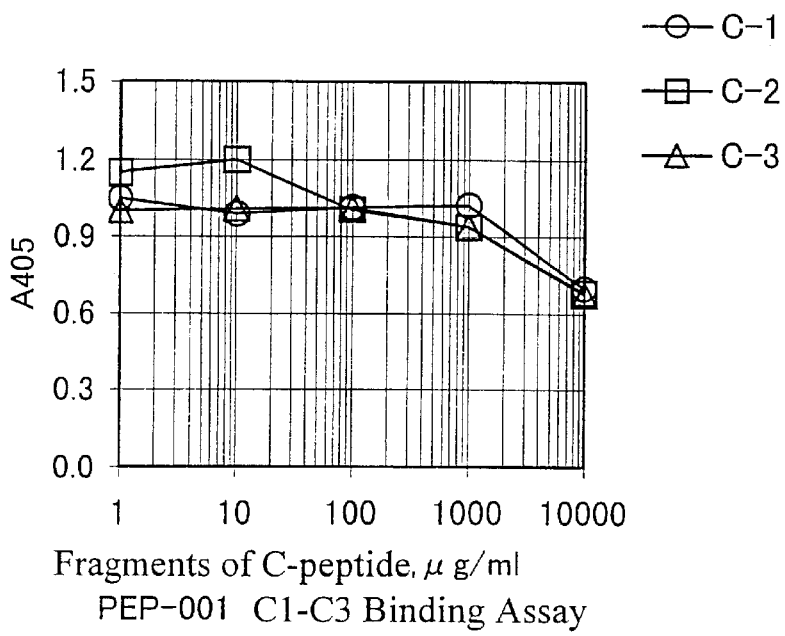
Figure 6:
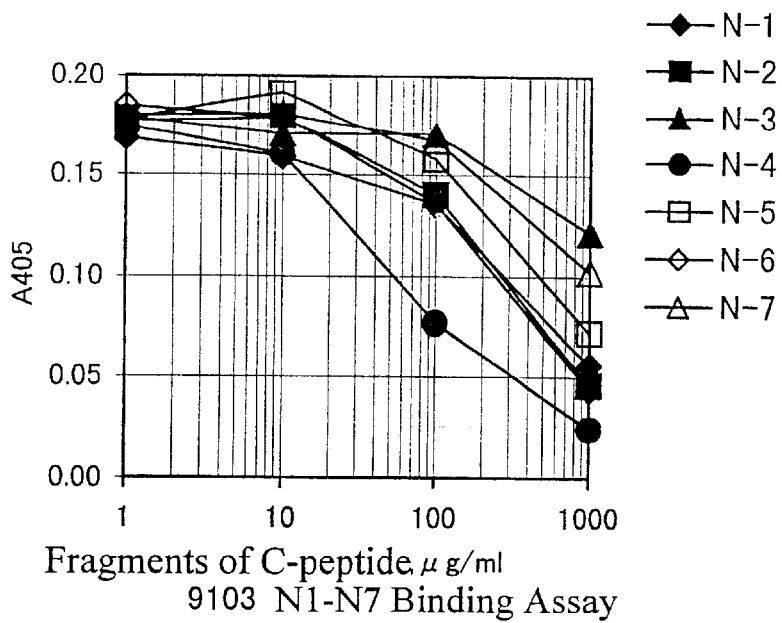
FIG. 6 shows the results of binding inhibition assay for anti-human C-peptide antibody 9103 using various fragments of human C-peptide.
Figure 6:
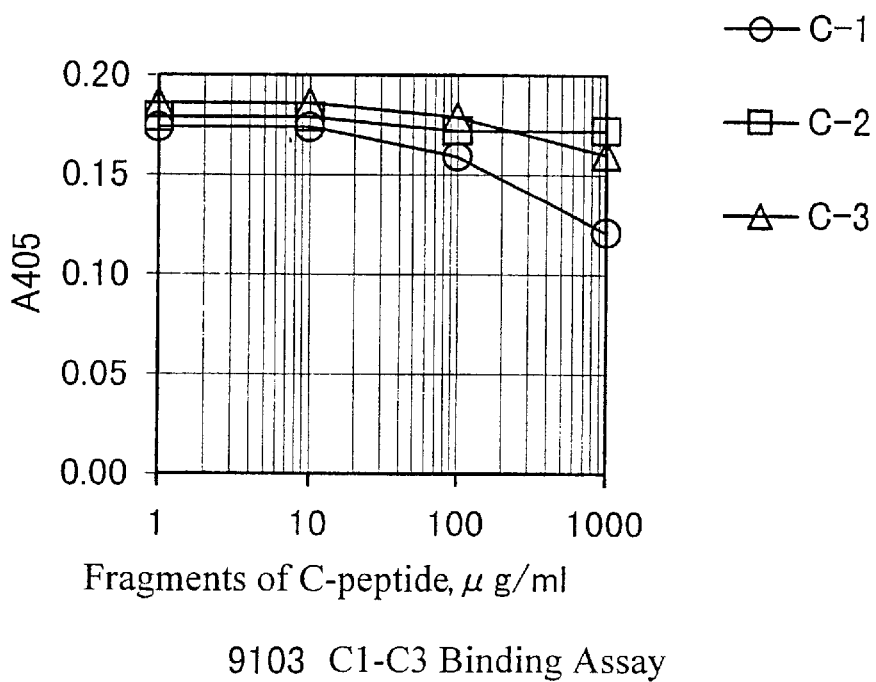

The present invention provides a sandwich immunoassay for measuring human C-peptide wherein first and second anti-human C-peptide antibodies which recognize different epitopes are used.

The first anti-human C-peptide antibody used in the immunoassay according to the present invention is one which recognizes an epitope existing in the region from 1st to 10th amino acid from the N-terminal of human C-peptide (The 10th amino acid residue, for example, from the N-terminal is hereinafter indicated as "10a.a." for convenience. The positions of amino acids will hereinafter be indicated in the same manner. Further, for example, the region from 1st to 10th amino acid residue from the N-terminal of human C-peptide is herein after indicated as "1–10a.a." for convenience. The regions in C-peptide will hereinafter be indicated in the same manner). The first antibody preferably recognizes an epitope existing in 1–8a.a., more preferably an epitope existing in 1–8a.a. including at least a part of 1–3a.a. The term "recognize an epitope" means that the antibody undergoes antigen-antibody reaction with the epitope thereby binding to the epitope. The first antibody preferably does not substantially recognize human C-peptide having Arg-Arg-attached to the N-terminal thereof (residues 31–63 of SEQ ID NO:1) (hereinafter referred to as "Arg-Arg'C-peptide"). The term "does not substantially recognize" means that the cross-reactivity of the first antibody to Arg-Arg-C-peptide is not more than 10% when the concentration of Arg-Arg-C-peptide is 5 ng/ml. The cross-reactivity is preferably not more than 5%, more prefereably more than 1%. The cross-reactivity of the first antibody to Arg-Arg-C-peptide is determined by first preparing a calibration curve by the method of the present invention in a conventional manner using different known concentrations of human C-peptide solutions as samples, and measuring the apparent concentration of Arg-Arg-C-peptide solution whose actual concentration is known (5 nl/ml). The cross-reactivity of the immunoassay to Arg-Arg-C-peptide is the percentage of the apparent concentration measured based on the calibration curve to the actual concentration of Arg-Arg-C-peptide, the the proviso that the actual concentration is compensated so as to compensate the difference in molecular weights between C-peptide and Arg-Arg-C-peptide by multiplying the actual concentration by the ratio of molecular weights (see Example 4 below). It should be noted that the cross-reactivity of the antibody to Arg-Arg-C-peptide can be measured by using Arg-Arg-C-peptide to which Lys-Arg is attached at the C-terminal (i.e., "modified C-peptide" used in Example 3 below, residues 31–65 of SEQ ID NO:1) because the first antibody recognizes an epitope existing in 1–10a.a. region and so the precise structure of the C-terminal of the peptide does not inflkuence on the binding of the first antibody to the peptide. The first antibody is preferably a monoclonal antibody in view of reproducibility and specificity. Antigen-binding fragments such as Fab fragment and F(ab')$_2$ fragment of the first antibody may also be used in place of the first antibody. The first antibody of the antigen-binding fragment thereof is not immobilized, but used in free state.

The first antibody may be obtained by a method essentially known in the art. For example, anti-human C-peptide antibodies, preferably monoclonal antibodies, are produced by a conventional method well-known in the art, and the obtained antibodies are then examined for their corresponding epitopes. The corresponding epitope of an antibody may be determined by binding inhibition assay using a series of fragments of human C-peptide as exemplified in Example 5 described below. If antigen-antibody reaction between the antibody to be tested and human C-peptide is concentration-dependently inhibited by addition of a known amount of a polypeptide fragment, the antibody to be tested recognizes an epitope existing in the added polypeptide fragment. Thus, by using a polypeptide fragment consisting of at least five consecutive amino acids in the region of 1–10a.a. of human C-peptide as a competitor in the binding inhibition assay, the antibody which can be used as the first antibody can be selected. From the anti-human C-peptide antibodies, those which recognize epitopes existing in the region from 1–10a.a. of human C-peptide are selected in this manner and may be used as the first antibody in the method of the present invention. It should be noted that it is not necessary to determine the epitope exactly, but the first antibody may be selected by determining whether the epitope recognized by the antibody exist in the region of 1–10a.a. The first antibody which does not recognize human C-peptide having Arg-Arg-attached to the N-terminal thereof may also be selected in the similar manner. That is, such an antibody may be selected by excluding those which recognize human C-peptide having Arg-Arg- attached to the N-terminal thereof in the competition immunoassay described above, using a polypeptide fragment including the N-terminal of human C-peptide, to which Arg-Arg- is attached, is used as the competitor. Alternatively, the first antibody may also be obtained by using as an immunogen a peptide fragment having at least five consecutive amino acid in the region of 1-10a.a. attached to a protein carrier such as KLH or BSA, and by selecting the antibodies which recognize the peptide fragment used as the immunogen.

Anti-human C-peptide monoclonal antibodies are commercially available. Among these commercially available monoclonal antibodies, those which recognize epitopes in 1–10a.a. of human C-peptide may conveniently be employed as the first antibody in the method of the present invention. Anti-human C-peptide monoclonal antibody 9101 commercially available from Medix Biochemica is an example of the commercially available monoclonal antibodies which can be used as the first antibody in the method of the present invention.

The antigen-binding fragments of the first antibody may be obtained by the methods well-known in the art. That is, the Fab fragment can be obtained by digesting the first antibody with papain and the F(ab')$_2$ fragment can be obtained by digesting the first antibody with pepsin.

The second antibody used in the sandwich immunoassay according to the present invention recognizes an epitope existing in 1–16a.a. of the human C-peptide. As shown in Examples below, by using an antibody which recognizes an epitope existing in 1–16a.a. of the human C-peptide, cross-reactivity to human proinsulin is much more decreased when compared to the cases where an antibody which recognizes an epitope existing in the C-terminal half of human C-peptide is used as the second antibody. This phenomenon was originally discovered by the present inventors. In view of reproducibility and specificity, the second antibody is also preferably a monoclonal antibody.

To carry out sandwich immunoassay, it is necessary that the second antibody recognize an epitope which is different from the epitope recognized by the first antibody, and that both the first and second antibodies can simultaneously bind to human C-peptide. If two antibodies can simultaneously bind to human C-peptide, it is regarded in the present invention that the two antibodies recognize different epitopes even if the region of the epitopes partly overlap each other.

Antigen-binding fragments such as Fab fragment and F(ab')$_2$ fragment of the first antibody may also be used in place of the second antibody. Such fragments may be obtained by the methods well-known in the art as mentioned above.

The second antibody may be obtained as follows: First, anti-human antibodies which recognize epitopes existing in 1–16a.a. of human C-peptide molecule are obtained. These antibodies may be obtained in the similar manner as described above for obtaining the first antibody, using a polypeptide fragment consisting of at least 5 consecutive amino acids in 1–16a.a. of human C-peptide as a competitor in the binding inhibition assay, or as an immunogen bound to a protein carrier. It should be noted that it is not necessary to determine the epitope exactly, but the second antibody may be selected by determining whether the epitope recognized by the antibody exist in the region of 1–16a.a. Then those antibodies which can bind to human C-peptide simultaneously with the first antibody are selected. This can be carried out by checking whether human C-peptide can be measured by a usual sandwich immunoassay using the first antibody and the antibody which is a candidate as the second antibody.

Among the commercially available monoclonal antibodies, those which recognize epitopes in 1–16a.a. of human C-peptide and which can bind to human C-peptide simultaneously with the first antibody may conveniently be employed as the second antibody in the method of the present invention. When the first antibody is anti-human C-peptide monoclonal antibody 9101 commercially available from Medix Biochemica, anti-human C-peptide monoclonal antibody 9103 commercially available from Medix Biochemica and anti-human C-peptide monoclonal antibody CPT-3-F11 commercially available from Dako may be employed as the second antibody.

Except that the above-described characteristic first and second antibodies are used, and that the second antibody is immobilized, the sandwich immunoassay according to the present invention may be carried out in the conventional way. In the following description (except for the Examples below), unless otherwise specified or unless otherwise apparent from the context, the term "antibody" means antibody or an antigen-binding fragment thereof.

The second antibody is immobilized on a solid support. As experimentally shown in the Examples below, the cross-reactivity of the immunoassay to human proinsulin is smaller in cases where the second antibody is immobilized and the first antibody is free than in the cases where the first antibody is immobilized and the second antibody is free. The solid support per se is well-known in the art and any solid supports conventionally used in immunoassays may be employed. Thus, the solid support may preferably be made of a polymer such as polystyrene, polyethylene, Sepharose (Pharmacia), cellulose or the like. Latex particles coated with ferrite, which have magnetism may also preferably be used as the solid support. The shape of the solid support is not important and preferably be one with which the immobilization of the antibody on the surface thereof may easily be carried out, and the immune complex may easily be separated from the reaction mixture and the non-reacted antibody after the immunological reactions. Thus, the solid support may preferably be in the form of magnetic particles. Alternatively, the inner wall of a well in a plastic microplate may also preferably be used as the solid support. In view of ease of handling, storage stability, ease of separation and the like, use of magnetic particles such as latex particles coated with ferrite is especially preferred.

To quantify the immune complex, it is preferred to label the first antibody which is not immobilized on the solid support. Labeled antibodies are well-known in the art, and any of the labels conventionally employed in immunoassays may be employed. Thus, as the label, radioactive isotopes, enzymes and fluorescent substances may preferably be employed. Examples of the radioactive isotopes include $^{125}$I, $^{131}$I and the like. Examples of the enzymes include peroxidase, β-galactosidase, alkaline phosphatase and the like. As the substrates for the enzyme reactions, o-nitrophenyl-β-D-galactopyranoside, p-nitrophenyl phosphate, AMPPD (disodium 3-[4-methoxyspiro(1,2-dioxetane-3,2'-tricyclo[3,3,1,1$^{3,7}$]decane)-4-yl]phenyl phosphate) and the like may be employed. As the fluorescent substance, fluorescein isothiocyanate (FITC) and the like may be employed. These labels may be quantified by the conventional methods well-known in the art, thereby the formed immune complex is quantified. In a preferred mode of the present invention, alkaline phosphatase-bound antibody is used as the enzyme-labeled antibody, and AMPPD which is a chemiluminescent substance is used as the substrate for the enzyme reaction.

As is well-known, labeling of the first antibody is not mandate to attain the quantification of the immune complex. The immune complex may also be quantified by reacting a labeled third antibody with the immune complex on the solid support, which third antibody recognizes the first antibody which is not immobilized.

Using the above-described first and second antibodies, the sandwich immunoassay may be carried out in a conventional way. Thus, the sandwich immunoassay may be carried out either by one-step method or by two-step method. In the one-step method, the first and second antibodies, and human C-peptide contained in the sample are simultaneously reacted. After washing, the immune complex bound to the solid support is quantified. This method has an advantage that the immunological reactions are carried out in one step, so that the operations are simple and the time needed for the immunoassay is short. In the two-step method, the human C-peptide contained in the sample is first reacted with the immobilized second antibody. After washing, the first antibody which is not immobilized is then reacted with the human C-peptide captured on the solid support through the second antibody. After washing, the immune complex bound to the solid support is quantified. This two-step method has an advantage that cross-reactivity to human proinsulin is lower than the one-step method.

The immunological reactions between one of the antibodies and human C-peptide in the sample may be carried out at a temperature and for a period of time under which immune complex between the antibody and human C-peptide is sufficiently formed. For example, the immunological reactions may be carried out at a temperature between room temperature to 37° C. for not less than about 5 minutes, preferably for 7 to 30 minutes, or at 4° C. overnight, as in the conventional sandwich immunoassays.

The buffer used for the immunological reactions or for dilution may be any buffers which are conventionally used in immunoassays. Examples of such buffers include PBS, 50 mM Tris buffer (pH7.2) containing or not containing bovine serum albumin (BSA) and 50 mM MES buffer (pH6.8). The buffer may contain about 0.1% of sodium azide in order to prevent growth of bacteria.

The sandwich immunoassay according to the present invention gives high detection sensitivity and low cross-reactivity to human proinsulin and split type proinsulin (i.e., proinsulin lacking 31–32a.a. or 64–65a.a. in proinsulin). The cross-reactivity of the sandwich immunoassay of the present invention to human proinsulin may preferably be not more than 10%, more preferably not more than 5%, still more preferably not more than 1% when the actual concentration of human proinsulin is 50 ng/ml. The cross-reactivity of the immunoassay to human proinsulin is determined by first preparing a calibration curve by the method of the present invention in a conventional manner using different known concentrations of human C-peptide solutions as samples, and measuring the apparent concentration of human proinsulin solution whose actual concentration is known (50 ng/ml). The cross-reactivity of the immunoassay to human proinsulin is the percentage of the apparent concentration measured by the method of the present invention based on the calibration curve to the actual concentration of the human proinsulin, with the proviso that the actual concentration is compensated so as to compensate the difference in molecular weights between human C-peptide and human proinsulin by multiplying the actual concentration by the ratio of molecular weights (see Example 4 below). The detection sensitivity of the sandwich immunoassay according to the present invention is preferably not more than 0.05 ng/ml, more preferably not more than 0.02 ng/ml. The detection sensitivity is herein defined as 2S/N, which means the concentration of human C-peptide which gives the signal twice the signal (noise signal) yielded when the concentration of human C-peptide is 0 ng/ml.

The sample which is subjected to the sandwich immunoassay according to the present invention is not restricted, and may be, for example, body fluids such as blood, serum, plasma and urine, as well as feces, in which C-peptide may be secreted.

The present invention also provides a kit for easily carrying out the sandwich immunoassay according to the present invention. The kit according to the present invention includes a vessel containing the first antibody and a vessel containing the second antibody. The kit may further comprise one or more appropriate buffers for immunological reactions or for dilution, or concentrates thereof, the substrate for enzyme reaction or solution thereof, human C-peptide as a standard sample or solution thereof, and a vessel for carrying out the immunoassay or for dilution. Preferred examples of the buffer for suspending the anti-human C-peptide-bound particles include 50 mM Tris buffer (pH7.2) containing BSA, 150 mM sodium chloride and 0.1% sodium azide. Preferred examples of the buffer for dissolving the labeled anti-human C-peptide include the same buffer just mentioned above which further contains 0.3 mM zinc chloride.

In the kit according to the present invention, second antibody is immobilized on the solid support, and the first antibody is labeled. The first antibody may be in the form of a solution in an appropriate buffer or may be in the frozen-dried state. The second antibody may be in the frozen-dried state together with the solid support, or may be in the form of a suspension when the solid support is particles. The reagents contained in the kit according to the present invention may be provided separately in the respective vessels, each vessel containing a reagent in an amount for carrying out one immunoassay for one sample. Alternatively, each reagent may be contained in a vessel in an amount for carrying out immunoassays for a plurality of samples. In this case, each reagent is dividedly used in each immunoassay. In cases where each vessel contains a reagent in an amount for carrying out one immunoassay for one sample, the vessels containing the different reagents may be in the form of compartments integrally formed in a cartridge. In cases where the first and/or second antibodies are contained in the kit in frozen-dried state, a buffer such as those mentioned above suited for dissolving the antibodies may be included in the kit. The vessels containing the antibodies and other vessels included in the kit may be made of any materials as long as they do not interact with the antibodies and they do not adversely affect the enzyme reactions, chemiluminescent reactions and the like. If necessary, the surfaces of the vessels may be treated so as to prevent such interactions. Such surface treatments are well-known in the art. A manual carrying the instructions for using the kit is usually attached to the kit.

The present invention will now be described in more detail by way of examples thereof. In the examples, all % indicating concentrations of substances are by weight unless otherwise specified.

EXAMPLE 1

Materials and Measuring Method (1) Preparation of Anti-human C-peptide Antibody-bound Particles In 2.5 ml of 50 mM phosphate buffer (pH3.0), 1 mg of an anti-human C-peptide antibody (described below) was dissolved to prepare a sensitization solution. To 50 mg of magnetic particles (latex coated with ferrite, particle size: 2 $\mu$m, commercially available from Nippon Paint) ultrasonicated in 50 mM phosphate buffer (pH3.0), the sensitization solution was added and the resulting mixture was well mixed. The mixture was rotated at 25° C. for 1 hour to allow reaction. Thereafter, magnetic force was applied from the outside of the reaction vessel to attract the particles, and the reaction solution was removed by respiration, followed by washing the obtained particles with 50 mM MES buffer (pH5.5). The thus obtained sensitized magnetic particles were suspended in 50 mM MES buffer (pH5.5), and 1 ml of 5 mg/ml of aqueous solution of 1-ethyl-3-(3-dimethylaminopropyl)carbodiimide hydrochloric acid salt (Nacarai Tesque) was added, followed by allowing reaction at 25° C. for 30 minutes under rotation. The particles were then washed again while being attracted by magnetic force, and suspended in 50 mM Tris buffer (pH7.2) containing 0.1% sodium azide and the resulting mixture was stored at a low temperature until use. In use, the antibody-bound particles were suspended in 50 mM Tris buffer (pH7.2) containing 2% BSA, 150 mM sodium chloride and 0.1% sodium azide to a concentration of 0.03% (w/v) and the resulting suspension was used as particle suspension. The anti-human C-peptide monoclonal antibodies used for sensitization were 9101 (Medix Biochemica), 9103 (Medix Biochemica), CPT-3-F11 (Dako) and PEP-001 (Dako). The corresponding epitopes of these antibodies were determined as described in Example 5. As described later, the antibody 9101 can be used as the first antibody in the method of the present invention, the antibody 9103 and the antibody CPT-3-F11 can be used as the second antibody in the method of the present invention, and PEP-001 cannot be used in the present invention because its corresponding epitope is within the C-terminal half of human C-peptide.

(2) Preparation of Alkaline Phosphatase-labeled Anti-human C-peptide Antibodies

Each of the anti-human C-peptide antibodies described in (1) was bound to alkaline phosphatase (Oriental Yeast) by the method described in Yoshitake et al. (Yoshitake et al., J. Biochem. 1982, 92(5), 1413–1424) to prepare an enzyme-labeled antibody. The enzyme-labeled antibody was diluted with 50 mM MES buffer (pH6.8) containing 1% BSA, 150 mM sodium chloride, 0.3 mM zinc chloride and 0.1% sodium azide to a concentration of 0.2 $\mu$g/ml to obtain a labeled antibody solution.

(3) Standard Solution

Human C-peptide was diluted to optional concentrations with Lumipulse sample diluent (Fujirebio Inc.) and the dilutions were used as standard solutions.

(4) Measuring Method

As the measuring apparatus, fully automatic chemiluminescent immunoassay system Lumipulse Forte (Fujirebio Inc., hereinafter referred to as "Lumipulse Forte") was used, and the immunoassays were carried out according to one-step method and two-step method. The procedures of the measurements were as follows:

(4-1) One-step Method

As the reaction vessel for immunoassay, the immunological reaction cartridge for Lumipulse Forte was used. In the immunological reaction bath in the cartridge, 50 $\mu$l of the particle suspension was placed, and 120 $\mu$l of the labeled antibody solution was placed in the reagent bath. After sealing the bathes with aluminum foil, the cartridge was set in a cassette. Lumipulse washing solution (Fujirebio Inc., hereinafter referred to as "washing solution") consisting of 10 mM Tris buffer and 0.1% polyoxyethylene(10) octylphenyl ether, Lumipulse substrate solution (Fujirebio Inc., hereinafter referred to as "substrate solution") containing as a major component chemical luminescence substrate AMPPD, and the cassette were set in the prescribed positions in Lumipulse Forte. The operations and measurements were carried out automatically under the control by the computer program equipped in Lumipulse Forte. The details are as follows:

The standard solution or sample is set in a sample rack. The sample rack is set to a prescribed position and the order of initiation of measurement operation is input in the computer program so as to start the measurement. The measurement is carried out in accordance with the measuring method, number of samples, amounts of reagents and order of measuring steps, which were designated in the computer program. Upon initiation of the measurement, the sample rack is firstly moved to the sample addition position in the apparatus. Simultaneously, the immunological reaction cartridge is taken out of the cassette and is moved to a linear reaction line kept at 37° C. The reaction line includes a site for sucking reaction solution, a site for adding the washing solution, magnets for attracting the particles by magnetic force, a mixer for stirring the reaction mixture, and a site for adding labeled antibody solution and substrate solution, and each operation is carried out under the control of the computer program.

A sampling tip mounted on the tip of the arm for adding sample sucks 20 $\mu$l of the sample. The sampling tip is then moved to the reagent bath in the immunological reaction cartridge and sucks 50 $\mu$l of the labeled antibody. The tip is then moved to the immunological reaction bath in the cartridge and the sucked sample and reagent are discharged thereinto. Then suction and discharge are repeated to well mix the reaction mixture. The reaction mixture is incubated at 37° C. for 16 minutes in the immunological reaction bath. During this period, the cartridge is intermittently moved to the washing site along the reaction line at an interval of 30 seconds. Before the washing site, magnets are arranged in the both sides of the reaction line so as to attract the particles. Then a respiration nozzle is moved into the reaction bath and sucks the remaining reaction solution so as to completely separate the particles from the reaction solution.

The particles separated from the reaction solution go apart from the magnets and the washing solution is added thereto from a washing solution nozzle. The particles are well mixed with the washing solution by stirring and again attracted by magnetic force so as to be separated from the washing solution. A cycle of attraction by magnetic force, removal of remaining solution, addition of washing solution, stirring and attraction of particles is repeated 7 times to finish the washing operation. After completion of the washing step, 200 $\mu$l of the substrate solution is added and well mixed with the particles. The mixture is incubated at 37° C. for 4 minutes and 30 seconds in the reaction line. The cartridge is then moved to the counting site and the amount of luminescence emitted during 30 seconds is measured. The concentration of a sample was calculated based on a calibration curve prepared by measuring amounts of chemiluminescence of standard human C-peptide with known concentrations.

(4-2) Two-step Method

As the reaction vessel for immunoassay, the immunological reaction cartridge for Lumipulse Forte was used. In the immunological reaction bath in the cartridge, 50 μl of the particle suspension was placed, and 120 μl of the labeled antibody solution was placed in the reagent bath. After sealing the bathes with aluminum foil, the cartridge was set in a cassette. The washing solution, the substrate solution and the cassette were set in the prescribed positions in Lumipulse Forte. The operations and measurements were carried out automatically under the control by the computer program equipped in Lumipulse Forte. The details are as follows:

The standard solution or sample is set in a sample rack. The sample rack is set to a prescribed position and the order of initiation of measurement operation is input in the computer program so as to start the measurement. The measurement is carried out in accordance with the measuring method, number of samples, amounts of reagents and order of measuring steps, which were designated in the computer program. Upon initiation of the measurement, the sample rack is firstly moved to the sample addition position in the apparatus. Simultaneously, the immunological reaction cartridge is taken out of the cassette and is moved to a linear reaction line kept at 37° C. The reaction line includes a site for sucking reaction solution, a site for adding the washing solution, magnets for attracting the particles by magnetic force, a mixer for stirring the reaction mixture, and a site for adding labeled antibody solution and substrate solution, and each operation is carried out under the control of the computer program.

A sampling tip mounted on the tip of the arm for adding sample sucks 30 μl of the sample. The tip is then moved to the reaction bath and 20 μl aliquot of the sucked sample is discharged thereinto. The discharged sample is well mixed with the particles by vortex mixing. The reaction mixture is incubated at 37° C. for 8 minutes in the reaction bath. During this period, the cartridge is intermittently moved to the washing site along the reaction line at an interval of 30 seconds.

After completion of the washing step, labeled antibody nozzle sucks 50 μl of the labeled antibody solution in the reagent bath and discharge it into the immunological reaction bath. The labeled antibody and the particles are well mixed by vortex mixing and the mixture is incubated at 37° C. for 8 minutes. During this period, the cartridge is intermittently moved to the washing site along the reaction line at an interval of 30 seconds. After completion of the washing step, 200 μl of substrate solution is added and well mixed with the particles. The mixture is incubated at 37° C. for 4 minutes and 30 seconds in the reaction line. The cartridge is then moved to the counting site and the amount of luminescence emitted during 30 seconds is measured. The concentration of a sample was calculated based on a calibration curve prepared by measuring amounts of luminescence of standard human C-peptide with known concentrations.

EXAMPLE 2

Response to C-peptide and Detection Sensitivity

Using all of the 12 combinations of the antibody-bound particles/labeled antibody, the antibody being one of the four antibodies described in Example 1(1), excluding the combinations wherein the same antibody is used as the antibody bound to the particles and the labeled antibody, immunoassays were carried out by one-step method and two-step method as described above. Thus, totally 24 immunoassays were carried out. In each immunoassay, 2S/N values were measured. As mentioned above, 2S/N value means the antigen concentration which yields the signal that is twice the signal (noise signal) obtained when the antigen is not added (i.e. antigen concentration is 0 ng/ml). The 2S/N values were used as the indices for comparing the detection sensitivities of the immunoassays employing different combinations of the antibodies. The results are shown in Tables 1 and 2 below.

TABLE 1

2S/N Values (One-step Method)

| | | Labeled Antibody | | | |
|---|---|---|---|---|---|
| | | 9101 | PEP-001 | 9103 | CPT-3F-11 |
| Antibody Immobilized on Particles | 9101 | — | ND | 0.222 | 0.008 |
| | PEP-001 | ND | — | 0.781 | 0.191 |
| | 9103 | 0.117 | 0.009 | — | ND |
| | CPT-3F-11 | 0.008 | 0.012 | ND | — |

—: not conducted
ND: lower than detection sensitivity

TABLE 2

2S/N Values (Two-step Method)

| | | Labeled Antibody | | | |
|---|---|---|---|---|---|
| | | 9101 | PEP-001 | 9103 | CPT-3F-11 |
| Antibody Immobilized on Particles | 9101 | — | ND | 0.110 | 0.009 |
| | PEP-001 | ND | — | 0.591 | 0.271 |
| | 9103 | 0.167 | 0.018 | — | ND |
| | CPT-3F-11 | 0.005 | 0.006 | ND | — |

—: not conducted
ND: lower than detection sensitivity

EXAMPLE 3

Cross-reactivity to Modified C-peptide

With an immunoassay system which can well recognize the terminal region of C-peptide, it is expected that its response to proinsulin and split type proinsulin may be decreased. To check this, a modified C-peptide which is a polypeptide consisting of human C-peptide having Arg-Arg bound to its N-terminal and Lys-Arg bound to its C-terminal as prepared (residues 31–65 of SEQ ID NO:1. As noted, Arg-Arg is the sequence immediately upstream of the N-terminal of the C-peptide segment in human proinsulin, and Lys-Arg is the sequence immediately downstream of the C-terminal of the C-peptide segment in human proinsulin. The modified C-peptide was diluted with the sample diluent to a concentration of =ng/ml. This sample solution was subjected to the one-step method and two-step method described in Example 1. The apparent concentration of the modified C-peptide was calculated based on the calibration curve prepared by measuring amounts of chemiluminescence of standard antigen (human C-peptide) with known concentrations. The calibration curve of each immunoassay was prepared in the same manner as in Example 4 below. The thus measured concentration was divided by the actual concentration (i.e., 5 ng/ml), which was defined as the "cross-reactivity' here. The results are shown in Tables 3 and 4.

TABLE 3

Cross-reactivity (%) to Modified C-peptide (One-step Method)

| | | Labeled Antibody | | | |
|---|---|---|---|---|---|
| | | 9101 | PEP-001 | 9103 | CPT-3F-11 |
| Antibody Immobilized on Particles | 9101 | — | — | <0.5 | 9.3 |
| | PEP-001 | — | — | 35.0 | 98.5 |
| | 9103 | <0.5 | 58.2 | — | — |
| | CPT-3F-11 | 0.5 | 62.7 | — | — |

—: not conducted

TABLE 4

Cross-reactivity (%) to Modified C-peptide (Two-step Method)

| | | Labeled Antibody | | | |
|---|---|---|---|---|---|
| | | 9101 | PEP-001 | 9103 | CPT-3F-11 |
| Antibody Immobilized on Particles | 9101 | — | — | <0.7 | 1.7 |
| | PEP-001 | — | — | 38.3 | 80.0 |
| | 9103 | <0.5 | 38.6 | — | — |
| | CPT-3F-11 | 0.5 | 53.2 | — | — |

—: not conducted

As shown in Tables 3 and 4, with all of the combinations where in the antibody 9101 is used, the cross-reactivity to the modified C-peptide was less than 0.5% to 9.3%, so that the immunoassay systems can clearly distinguish C-peptide from the modified C-peptide.

EXAMPLE 4

Cross-reactivity to Proinsulin

Figure 8:
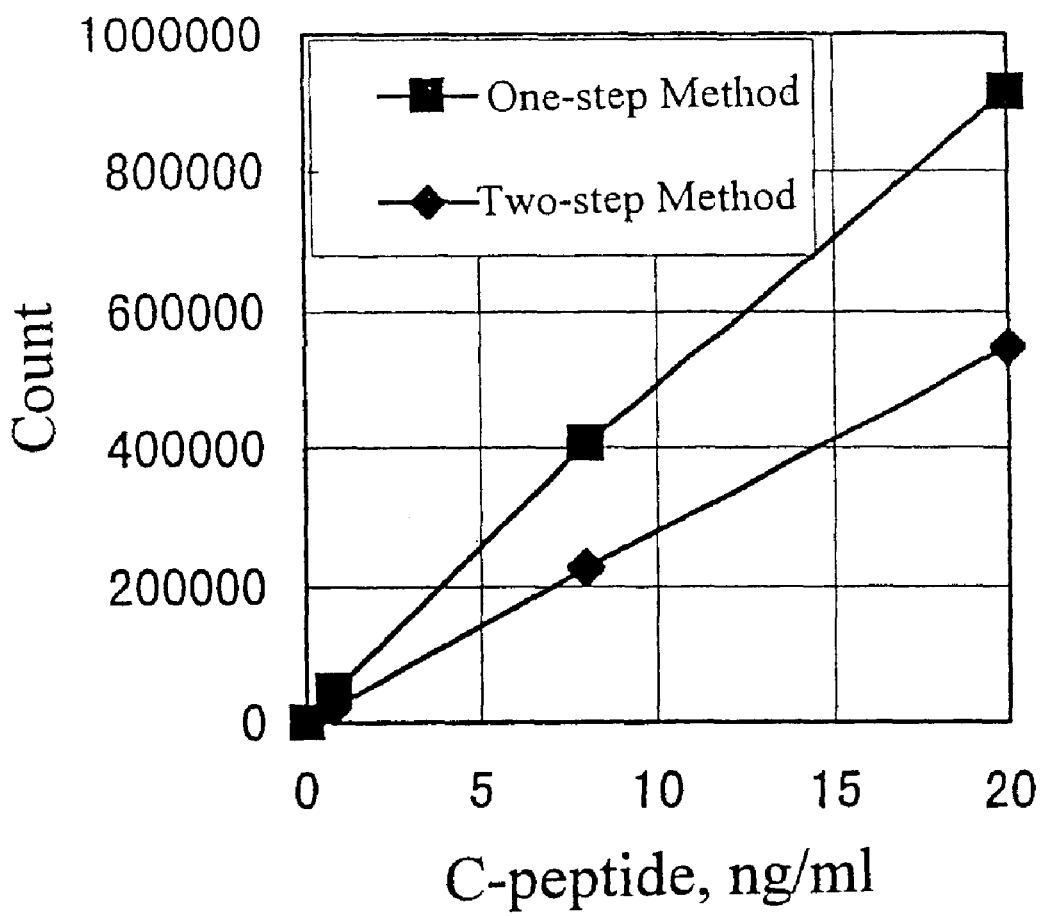
FIG. 8 shows calibration curves prepared in Example 4 by the one-step method and the two-step method, wherein the antibody 9101 was used as the labeled antibody and the antibody CPT-3-F11 was used as the second antibody immobilized on magnetic particles.

Using proinsulin solution as the sample, immunoassays were carried out as described in Example 1. The calibration curve in each immunoassay was prepared as follows: Human C-peptide solutions having concentrations of human C-peptide of 0,0.8, 8 and 20 ng/ml, respectively, were prepared and used as the standard solutions. Using 20 μl of each of these standard solutions, each immunoassay was carried out by the method described in Example 1. The calibration curves obtained in the one-step method and the two-step method using the antibody 9101 as the labeled antibody and the antibody CPT-3F-11 as the second antibody are shown in FIG. 8.

Human proinsulin was diluted with the sample diluent to a concentration of 50,200 or 400 ng/ml. Using these solutions as samples, immunoassays were carried out by the method as described in Example 1. For example, the measured counts of chemiluminescence of the samples having the concentrations of 50,200 and 400 ng/ml, respectively, of human proinsulin were 4139, 51,337 and 118,126, in the one-step method, and were 4401, 42,493 and 99,434, respectively, in the two-step method, both methods using the antibody 9101 as the labeled antibody and the antibody CPT-3F-11 as the second antibody. The concentrations corresponding to these counts were read from the respective calibration curves. The each read concentration was divided by the actual concentration (compensated as described below) and the calculated percentage was defined as the cross-reactivity. Since the molecular weight of human proinsulin is 9494 and that of human C-peptide is 3019, the actual concentrations of the human proinsulin were compensated so as to reflect this difference in the molecular weights by multiplying the actual concentration by the ratio of the molecular weights. Thus, for example, the concentration of proinsulin of 50 ng/ml was compensated to 15.9 ng/ml.

The results are shown in Tables 5 and 6.

TABLE 5

Cross-reactivity (%) to Human Proinsulin (One-step Method)

| Antibody Immobilized on Particles | Concentration of Added Proinsulin (mg/ml) | Labeled Antibody | | | |
|---|---|---|---|---|---|
| | | 9101 | PEP-001 | 9103 | CPT-3-F11 |
| 9101 | 50 | — | — | 19.7 | 19.6 |
| | 200 | — | — | 18.1 | 17.8 |
| | 400 | — | — | ≧15 | 11.7 |
| PEP-001 | 50 | — | — | ≧120 | ≧120 |
| | 200 | — | — | ≧30 | ≧30 |
| | 400 | — | — | ≧15 | ≧15 |
| 9103 | 50 | 3.2 | 58.0 | — | — |
| | 200 | 5.8 | ≧30 | — | — |
| | 400 | 6.9 | ≧15 | — | — |
| CPT-3-F11 | 50 | 0.9 | 56.8 | — | — |
| | 200 | 2.6 | ≧30 | — | — |
| | 400 | 3.0 | ≧15 | — | — |

—: not conducted

TABLE 6

Cross-reactivity (%) to Human Proinsulin (Two-step Method)

| Antibody Immobilized on Particles | Concentration of Added Proinsulin (mg/ml) | Labeled Antibody | | | |
|---|---|---|---|---|---|
| | | 9101 | PEP-001 | 9103 | CPT-3-F11 |
| 9101 | 50 | — | — | 12.8 | 10.7 |
| | 200 | — | — | 9.8 | 11.8 |
| | 400 | — | — | 8.4 | 12.1 |
| PEP-001 | 50 | — | — | ≧120 | ≧120 |
| | 200 | — | — | ≧30 | ≧30 |
| | 400 | — | — | ≧15 | ≧15 |
| 9103 | 50 | 2.3 | 65.2 | — | — |
| | 200 | 4.4 | ≧30 | — | — |
| | 400 | 6.8 | ≧15 | — | — |
| CPT-3-F11 | 50 | 0.4 | 41.1 | — | — |
| | 200 | 1.2 | ≧30 | — | — |
| | 400 | 1.4 | ≧15 | — | — |

—: not conducted

As shown in Tables 5 and 6, when the antibody 9101 was used as the antibody bound to the particles or as the labeled antibody, although the cross-reactivity varied depending on the counterpart antibody, the smallest cross-reactivity was as small as 0.4%. It can also be seen from Tables 5 and 6 that the cross-reactivities were generally smaller in the two-step method than in one-step method.

EXAMPLE 5

Determination of Epitopes of Antibodies by ELISA

To determine the epitopes of the four antibodies, ELISA was carried out using an ELISA plate on which human C-peptide was immobilized. The details were as follows:
(1) Preparation of Plate Sensitized with Human C-peptide Human C-peptide was dissolved in 0.1 M phosphate buffer (pH7.0) to a concentration of 0 to 10 μg/ml. To the wells of a microplate (Microwell Module (Nunc)), the above-mentioned human C-peptide solutions having varying concentrations, respectively, in an amount of 0.1 ml/well, and the plate was left to stand overnight at 4° C. The C-peptide solution in each well was then discarded and the wells were well washed with Lumipulse washing solution. Then 0.3 ml of 50 mM Tris buffer (pH7.0) containing 2% BSA and 0.1% sodium azide was placed in each well and the plate was incubated at 37° C. overnight. The plate was then stored at 4° C. until use.

(2) Verification Test for Binding Inhibition by Free Human C-peptide

Human C-peptide solutions in 50 mM MES buffer containing 1% BSA, 1 mM $MgCl_2$ and 0.1% $NaN_3$ having varying concentrations of 0 to 10 μg/ml were prepared, and added to the wells of the microplate prepared in (1) in an amount of 0.1 ml/well.

Then solution of labeled antibody 9101 or labeled antibody CPT3F11in the MES buffer just mentioned above having a concentration of 0.0 to 10 μg/ml was added to the wells in an amount of 0.1 ml/well. After mixing the mixture by lightly shaking the plate, the plate was incubated at 25° C. for 1 hour to allow immunological reaction. After the reaction, the wells were well washed with Lumipulse washing solution and 10 mM 4-nitrophenyl phosphate solution in 1.0 M diethanolamine buffer (pH10.0) containing 1 mM $MgCl_2$ was added to the wells in an amount of 0.1 ml/well. The plate was incubated at 25° C. for 30 minutes and absorbance at 405 nm was measured. From the measured absorbance, the binding ratio of each labeled antibody was calculated. The term "binding ratio" herein means the percentage of the absorbance measured when the concentration of the added human C-peptide solution was 0.1 to 10 μg/ml to the absorbance measured when the concentration of human C-peptide was 0 μg/ml (i.e., human C-peptide was not contained in the solution).

The results are shown in Tables 7 and 8. As shown in these tables, when the concentration of the added human C-peptide was 0 μg/ml, sufficient coloring was obtained, so that binding of the each labeled antibody to the immobilized human C-peptide was confirmed. In cases where a human C-peptide solution was added, the binding ratios decreased concentration-dependently as the concentrations of the added human C-peptide solutions increased. Thus, it was confirmed that the ELISA systems rightly worked.

TABLE 7

Verification Test for Binding Inhibition by Free Human C-peptide Using Labeled CPT3F11 Antibody

| | Concentration of Added C-peptide (μg/ml) | Concentration of CPT3F11 Antibody (μg/ml) | | |
|---|---|---|---|---|
| | | 0.0 | 0.1 | 1.0 | 10 |
| Absorbance | 0 | 0.000 | 1.523 | 1.940 | 2.171 |
| | 0.1 | 0.000 | 0.179 | 0.311 | 0.336 |
| | 1.0 | 0.000 | 0.026 | 0.062 | 0.059 |
| | 10 | 0.000 | 0.000 | 0.003 | 0.008 |
| Binding Ratio | 0 | 0.0 | 100.0 | 100.0 | 100.0 |
| | 0.1 | 0.0 | 11.8 | 16.0 | 15.5 |
| | 1.0 | 0.0 | 1.7 | 3.2 | 2.7 |
| | 10 | 0.0 | 0.0 | 0.2 | 0.1 |

TABLE 8

Verification Test for Binding Inhibition by Free Human C-peptide Using Labeled 9101 Antibody

| | Concentration of Added C-peptide (μg/ml) | Concentration of 9101 Antibody (μg/ml) | | |
|---|---|---|---|---|
| | | 0.0 | 0.1 | 1.0 | 10 |
| Absorbance | 0 | 0.000 | 1.262 | 1.689 | 1.983 |
| | 0.1 | 0.000 | 0.141 | 0.298 | 0.331 |
| | 1.0 | 0.000 | 0.013 | 0.042 | 0.051 |
| | 10 | 0.000 | 0.000 | 0.001 | 0.001 |
| Binding Ratio | 0 | 0.0 | 100.0 | 100.0 | 100.0 |
| | 0.1 | 0.0 | 11.1 | 17.6 | 17.1 |
| | 1.0 | 0.0 | 1.0 | 2.5 | 2.6 |
| | 10 | 0.0 | 0.0 | 0.0 | 0.1 |

(3) Binding Inhibition by Fragments of Human C-peptide (1)

Ten fragments of human C-peptide were synthesized. The synthesized fragments are shown in Table 9 below. The positions of the fragments in human C-peptides peptides are also shown in FIGS. 1 and 2.

TABLE 9

| Fragment Code | Position in Human C-peptide |
|---|---|
| N-1 | Arg-Arg-1-8a.a.*[1] |
| N-2 | 1-8a.a. |
| N-3 | 3-8a.a. |
| N-4 | 5-12a.a. |
| N-5 | 2-8a.a. |
| N-6 | 3-10a.a. |
| N-7 | 4-10a.a. |
| C-1 | 24-31a.a.-Lys-Arg*[2] |
| C-2 | 24-31a.a. |
| C-3 | 24-29a.a. |

*[1]Arg-Arg is bound to N-terminal of 1-8a.a.
*[2]Lys-Arg is bound to C-terminal of 24-31a.a.

Each of the fragments was dissolved in 50 mM MES buffer containing 1% BSA, 1 mM $MgCl_2$ and 0.1% $NaN_3$ to a concentration of 0 to 1 mg/ml, and the obtained solution was placed to the well in the plate prepared in Example 5(1) in an amount of 0.1 ml/well. Then the solution containing 0.1 μg/ml of labeled antibody 9101, CPT3F11, PEP-001 or 9103 in the same buffer as just mentioned above was added to the well. Thereafter, the same operations as in Example 5(2) were repeated and the absorbances at 405 nm were measured. The higher the binding ability of the labeled antibody to the fragment, the smaller the absorbance at 405 nm.

The results are shown in FIGS. 3–6. As shown in FIG. 4(A), the binding of labeled antibody 9101 to the immobilized C-peptide was concentration-dependently inhibited most when fragment N-3 or N-6 was added as a competitor. Since these fragments commonly contain 3–8a.a., the epitope of antibody 9101 was estimated to be 3–8a.a. Similarly, as shown in FIG. 6(A), the binding of labeled antibody 9103 to the immobilized C-peptide was concentration-dependently inhibited most when fragment N-4 was added as a competitor. Thus, the epitope of antibody 9103 was estimated to reside in 5–12a.a. As for antibody CPT3F11, the binding ability was not significantly and concentration-dependently inhibited by any of the fragments used, so that the epitope did not exist in the fragments used in this experiment. Determination of epitope of CPT3F11 will be described in the next section. From FIG. 5, it can be seen that the epitope of PEP-001 resides in C-terminal region of human C-peptide.

(4) Binding Inhibition by Fragments of Human C-peptide (2)

The same operations as in Example 5(3) were repeated except that the used fragments were shown in Table 10 below, and the used labeled antibody was antibody CPT3F 11 alone.

TABLE 10

| Fragment Code | Position in Human C-peptide |
|---|---|
| N-4 | 5-12a.a. |
| N-8 | 7-14a.a. |
| N-9 | 9-16a.a. |
| N-10 | 7-13a.a. |
| N-11 | 7-12a.a. |
| N-12 | 8-14a.a. |
| N-13 | 9-14a.a. |
| N-14 | 10-14a.a. |

Figure 7:
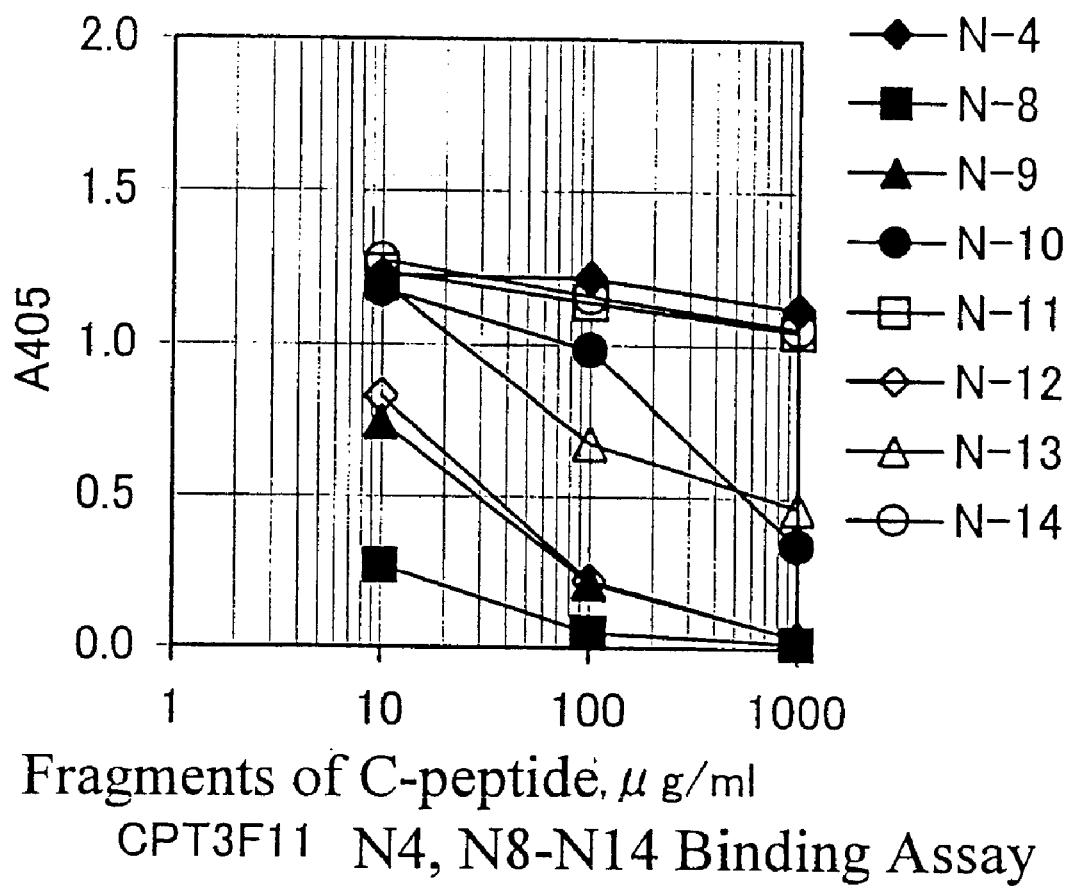
FIG. 7 shows the results of binding inhibition assay for anti-human C-peptide antibody CPT3F11 using various fragments of human C-peptide.

The results are shown in FIG. 7. As shown in FIG. 7, the binding to the immobilized C-peptide was not substantially inhibited by N-4, N-11 and N-14, while inhibited concentration-dependently by other fragments. The common sequence which the fragments that inhibited the binding has, and which does not exist in N-4, N-11 and N-14 is 9–13a.a. Thus, the epitope of antibody CPT3F11 was estimated to be 9–13a.a.

Thus, since the epitope of antibody 9101 is 3–8a.a., antibody 9101 can be employed as the first antibody in the immunoassay according to the present invention. Since the epitopes of antibody 9103 and antibody CPT3F11 exist in 5–12a.a. and 9–13a.a., respectively, both of which is within 1–16a.a. Further, as shown in Example 2, sandwich immunoassay for measuring human C-peptide can be carried out using the combination of 9101/9103 or 9101/CPT3F11, which means that antibodies 9101 and 9103 can simultaneously bind to human C-peptide molecule and that antibodies 9101 and CPT3F11 can simultaneously bind to human C-peptide molecule. Therefore, antibodies 9101 and CPT3F 11can be used as the second antibody in the immunoassay according to the present invention.

EXAMPLE 6

Immunoassay Kit for Measuring Human C-peptide

As an example of immunoassay kit for measuring human C-peptide, a kit including the vessels containing the following Reagents 1–4, respectively, was prepared.

Reagent 1: Suspension of antibody-bound particles, which contains 0.03% (w/v) of anti-human C-peptide antibody-bound particles in 50 mM Tris buffer (pH7.2) containing 150 mM sodium chloride, 2% BSA and 0.1% sodium azide.

Reagent 2: Labeled antibody solution containing 0.2 µg/ml of alkaline phosphatase-labeled anti-human C-peptide antibody in 50 mM MES buffer (pH6.8) containing 100 mM sodium chloride, 0.3 mM zinc chloride and 0.1% sodium azide.

Reagent 3: Standard C-peptide solution containing human C-peptide at an optional concentration in 50 mM Tris buffer (pH 7.2) containing 150 mM sodium chloride, 2% BSA and 0.1% sodium azide.

Reagent 4: Substrate solution containing 0.02% AMPPD in 50 mM diethanolamine buffer (pH 10.0) containing 0.1% sodium azide.

We claim:

1. A method for measuring human C-peptide comprising the steps of:
   (i) reacting human C-peptide contained in a sample, a first anti-human C-peptide antibody or an antigen-binding fragment thereof, and a second anti-human C-peptide antibody or an antigen-binding fragment thereof immobilized on a solid support to form an immune complex among three components;
   (ii) separating the formed immune complex from non-reacted antibodies and/or antigen-binding fragments thereof, and sample, and
   (iii) quantifying the separated immune complex;
   said first antibody recognizing an epitope existing in the region from residues 1–10 of SEQ ID NO:2 from the N-terminal of said human C-peptide; said second antibody recognizing an epitope existing in the region from residues 1–16 of SEQ ID NO:2 from the N-terminal of said human C-peptide; and said first and second antibodies recognizing different epitopes so that they can simultaneously bind to said human C-peptide.

2. The method according to claim 1, wherein said first antibody or the antigen-binding fragment thereof does not substantially recognize human C-peptide having Arg-Arg- bound to N-terminal thereof.

3. The method according to claim 1, wherein said solid support is magnetic particles.

4. The method according to claim 1, wherein said step (i) is carried out in one step such that said human C-peptide contained in a sample, said first anti-human C-peptide antibody or the antigen-binding fragment thereof, and said second anti-human C-peptide antibody or the antigen-binding fragment thereof are reacted simultaneously.

5. The method according to claim 1, wherein said step (i) is carried out in two steps such that said human C-peptide in the sample is first reacted with said second antibody or the antigen-binding fragment thereof immobilized on said solid support so as to form an immune complex therebetween thereby binding said human C-peptide to said solid support, and said first antibody or the antigen-binding fragment thereof is then reacted with said human C-peptide bound to said solid support after washing off human C-peptide which was not immobilized on said solid support.

6. The method according to claim 1, wherein said first antibody or the antigen-binding fragment thereof is labeled, and said step (iii) is carried out by quantifying the label bound to said solid support after washing off non-reacted labeled antibody or the antigen-binding fragment thereof.

7. The method according to claim 1, in which said first antibody and said second antibody are used.

8. The method according to any one of claims 1 to 7, wherein cross-reactivity of said method to human proinsulin is not more than 10%.

9. The method according to claim 8, wherein cross-reactivity of said method to human proinsulin is not more than 5%.

10. The method according to claim 9, wherein cross-reactivity of said method to human proinsulin is not more than 1%.

11. The method according to any one of claims 1 to 7, which has a detection sensitivity of human C-peptide of not more than 0.05 ng/ml.

12. A kit for measuring human C-peptide comprising:
   (a) a first vessel containing a first anti-human C-peptide antibody or an antigen-binding fragment thereof, which is labeled; and
   (b) a second vessel containing a solid support on which a second anti-human C-peptide antibody or an antigen-binding fragment thereof immobilized;
   said first antibody recognizing an epitope existing in the region from residues 1–10 of SEQ ID NO:2 from the N-terminal of said human C-peptide; said second antibody recognizing an epitope existing in the region from residues 1–16 of SEQ ID NO:2 from the N-terminal of said human C-peptide; and said first and second antibodies recognizing different epitopes so that they can simultaneously bind to said human C-peptide.

13. The kit according to claim 12, wherein said first antibody or the antigen-binding fragment thereof does not substantially recognize human C-peptide having Arg-Arg- bound to N-terminal thereof.

14. The kit according to claim 12, wherein said first and second vessels are in the form of compartments integrally formed in a cartridge.

15. The kit according to any one of claims 12 to 14, wherein said first vessel contains said first anti-human C-peptide antibody and said second vessel contains said second anti-human C-peptide antibody.

16. The kit according to any one of claims 12 to 14, wherein cross-reactivity to human proinsulin of immunoassay carried out by using said kit is not more than 10%.

17. The kit according to claim 16, wherein cross-reactivity to human proinsulin of immunoassay carried out by using said kit is not more than 5%.

18. The kit according to claim 17, wherein cross-reactivity to human proinsulin of immunoassay carried out by using said kit is not more than 1%.

19. The kit according to any one of claims 12 to 14, which attains a detection sensitivity of human C-peptide of not more than 0.05 ng/ml.

* * * * *

SEQUENCE LISTING

<160> NUMBER OF SEQ ID NOS: 2

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 31
<212> TYPE: PRT
<213> ORGANISM: Homo sapiens

<400> SEQUENCE: 2

-continued

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
                20                  25              30
```